United States Patent
Afriat et al.

(10) Patent No.: US 6,239,174 B1
(45) Date of Patent: *May 29, 2001

(54) EMULSION CONTAINING ASCORBIC ACID AND ITS USES IN THE COSMETICS AND DERMATOLOGICAL FIELDS

(75) Inventors: Isabelle Afriat, Paris; Florence Chanvin, Soisy/S/Seine, both of (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/145,611

(22) Filed: Sep. 2, 1998

(30) Foreign Application Priority Data

Sep. 2, 1997 (FR) .................................................. 97 10902

(51) Int. Cl.[7] ..................................................... A61K 31/34
(52) U.S. Cl. .............................................. 514/474
(58) Field of Search ..................... 424/401, 59; 252/309; 514/252, 529, 396, 557, 474

(56) References Cited

U.S. PATENT DOCUMENTS

| | | | |
|---|---|---|---|
| 4,720,353 | * | 1/1988 | Bell ........................................ 252/309 |
| 5,380,528 | * | 1/1995 | Alban et al. ........................... 424/401 |
| 5,443,760 | * | 8/1995 | Kasprzak ............................ 424/78.03 |
| 5,545,399 | * | 8/1996 | Lee et al. ................................ 424/59 |
| 5,559,149 | * | 9/1996 | Clum et al. ........................... 514/529 |
| 5,583,136 | * | 12/1996 | Yusuf et al. ........................... 514/252 |
| 5,656,280 | * | 8/1997 | Herb et al. ............................ 424/401 |
| 5,674,511 | * | 10/1997 | Kacher et al. ........................ 424/401 |
| 5,705,144 | * | 1/1998 | Harding et al. ......................... 424/59 |
| 5,804,203 | * | 9/1998 | Hahn et al. ........................... 424/401 |
| 5,843,417 | * | 12/1998 | Hanna et al. ........................ 424/70.7 |
| 5,853,741 | * | 12/1998 | Znaiden et al. ...................... 424/401 |
| 5,997,887 | * | 12/1999 | Ha et al. .............................. 424/401 |
| 5,997,890 | * | 12/1999 | Sine et al. ............................ 424/401 |

FOREIGN PATENT DOCUMENTS

| | | |
|---|---|---|
| 0 670 157 | 9/1995 | (EP) . |
| 0 755 674 | 1/1997 | (EP) . |
| 2 738 743 | 3/1997 | (FR) . |
| WO 94/09756 | 5/1994 | (WO) . |

* cited by examiner

Primary Examiner—William R. A. Jarvis
Assistant Examiner—Vickie Kim
(74) Attorney, Agent, or Firm—Oblon, Spivak, McClelland, Maier & Neustadt, P.C.

(57) ABSTRACT

A water-in-oil emulsion containing ascorbic acid and, as an emulsifier, a dimethiconecopolyol or an alkyldimethiconecopolyol, where the aqueous phase having a pH ranging from 6.1 to 7.5. This emulsion allows ascorbic acid to be stabilized and can be used, in particular, in the cosmetics and/or dermatological fields. The invention also relates to a cosmetic process for treating the skin using the emulsion.

26 Claims, No Drawings

EMULSION CONTAINING ASCORBIC ACID AND ITS USES IN THE COSMETICS AND DERMATOLOGICAL FIELDS

BACKGROUND OF THE INVENTION

1. Field of the Invention

The present invention relates to a water-in-oil (W/O) emulsion containing ascorbic acid, to the use of this emulsion for topically treating the skin, on the face, including the area around the eyes, on the body and on the scalp of human beings, as well as to a process for treating the skin topically using this emulsion.

2. Description of the Background

It has been sought for a long time to stabilize ascorbic acid, or vitamin C, in appropriate pharmaceutical presentations, on account of its beneficial properties. This is because ascorbic acid has many biological functions, such as the stimulation of collagen synthesis, the strengthening of skin tissues against external attacking factors, depigmentation, its anti-free-radical activity, and the compensation for vitamin E deficiency.

However, on account of its chemical structure (α-keto lactone), ascorbic acid is very sensitive to the influence of environmental parameters such as light, oxygen and water. This results in an unavoidable degradation over time of ascorbic acid in solution form leading to a loss of its activity. Moreover, degradation, even slight, of the ascorbic acid, causes yellowing of a composition containing it.

To reduce or delay the degradation of ascorbic acid in solution form, it has been recommended in U.S. Pat. No. 5,140,043 to introduce it into aqueous-alcohol solutions, formed of at least 80% water and having a pH of less than 3.5. However, repeated application of solutions of strongly acidic pH to the skin can disrupt the skin's equilibrium and in particular cause skin irritation.

Moreover, EP-A-670,157 describes the stabilization of vitamin C in a W/O emulsion having a pH of not more than 3.5 and containing, as emulsifier, a dimethicone-copolyol and/or an alkyldimethiconecopolyol. Such a W/O emulsion is better tolerated by users than an aqueous-alcoholic solution, since the aqueous acidic phase containing ascorbic acid is applied in small amount to the skin, in the form of fine droplets dispersed in the oil, which causes no skin irritation or burning. However, repeated application of a composition of acidic pH can have drawbacks for individuals with sensitive skin.

In addition, WO-A-95/28092 discloses stabilizing active agents, such as enzymes or vitamins, in a water-in-oil emulsion containing a high concentration of polyols and an emulsifier chosen from monoglycerides and polyglyceryl ricinoleate. However, the emulsions described in this application contain less than 10% water, and there is still a need for emulsions which can contain more water while at the same time maintaining good stability of the ascorbic acid.

While, it is Inown that the pH has an influence on the stability of ascorbic acid. Thus, the article by B.R. Hajratwala entitled "Stability of ascorbic acid", published in Revue Sciences Pharmaceutiques on Mar. 15, 1985, shows that the decomposition of ascorbic acid exhibits minima at pH 2.5–3 and at pH 6. However, all the tests presented in that article are carried out using simple solutions of ascorbic acid in water and a person skilled in the art cannot deduce therefrom the behavior of ascorbic acid in an emulsion, in which the interactions of the oils and the surfactants modify the environment appreciably and unpredictably. In addition, prior literature in the cosmetics field encourage those skilled in the art to use an acidic pH (see U.S. Pat. No. 5,140,043 and EP-A670157, mentioned above).

The need thus exists for a composition which can be used in the cosmetics and/or dermatological fields, in which ascorbic acid is stable and which causes no skin irritation after application, even for individuals with sensitive skin.

SUMMARY OF THE INVENTION

The present invention is based, in part, on the surprising discovery that stability of ascorbic acid is considerably improved by incorporating ascorbic acid, or a salt thereof, into a water-in-oil emulsion containing a silicone-based surfactant, where the aqueous phase of the emulsion has a pH of 5.5 to 7.5, and that such a composition is very well tolerated by human skin.

Accordingly, the present invention provides a water-in-oil emulsion containing ascorbic acid and comprising an aqueous phase dispersed in an oily phase using at least one silicone-based emulsifier, where the aqueous phase has a pH ranging from 5.5 to 8, preferably equal to 6.

Thus, it has been found, surprisingly, that, in contrast with the teaching of that article according to which ascorbic acid in solution behaves very differently in aerobic medium and in anaerobic medium, the degradation of ascorbic acid in an emulsion according to the invention is the same, whether the medium be aerobic or anaerobic.

In the emulsion according to the invention, the pH is preferably equal to or close to 6. This pH is close to the skin's pH; this results in great compatibility of the emulsion of the invention with the skin.

The emulsion according to the invention allows the degradation of ascorbic acid to be avoided and thus stabilizes it. Thus, another subject of the present invention is the use of the emulsion as defined above to stabilize ascorbic acid.

The present invention also provides a method of tonifying and regenerating skin, smoothing out fine lines on the skin, improving the complexion of skin, removing skin pigmentation mark, combating the harmful effects of UV radiation, and/or to strengthening skin tissues against environmental attack, by applying the inventive emulsion to skin.

A more complete appreciation of the invention and many of the attendant advantages thereof will be readily obtained as the same becomes better understood by reference to the following detailed description.

DETAILED DESCRIPTION OF THE PREFERRED EMBODIMENTS

The ascorbic acid concentrations in the emulsion of the invention are those used conventionally in the cosmetics and dermatological fields and, for example, from 0.01 to 20%, preferably from 0.1 to 10% and better still from 0.5 to 5%, of the total weight of the emulsion. These ranges include all specific values and subranges therebetween, including 0.02, 0.05, 0.2, 1, 2, 3, 8, 12, 15 and 18% by weight. The ascorbic acid may be in the form of a salt. Preferred salts are alkali and alkaline earth metal salts of ascorbic acid (e.g., sodium, potassium, magnesium and/or calcium salts).

The silicone-based emulsifier is a compound having at least one silicone moiety. The silicone-based emulsifier is preferably chosen from dimethiconecopolyols and alkyldimethicone-copolyols. These emulsifiers preferably comprise fully oxyethylenated polyether groups. However, it is also possible to use emulsifiers having partially oxyethylenated polyether groups.

Advantageously, the weight percentage of polyether relative to the total weight of the emulsifier is chosen from 1 to 50%, preferably from 15 to 35%, in the case of dimethicone-copolyols, and from 1 to 5%, preferably from 2 to 3%, in the case of alkyldimethicone-copolyols. These ranges include all specific values and subranges therebetween, including 4, 10, 20, 25, 30, 35,40 and 45% by weight.

As dimethicone-copolyol which can be used in the emulsion according to the invention, mention may be made of the mixture of dimethicone-copolyol and cyclomethicone sold under the name "Q2-3225C" by Dow Corning and the product sold under the name "SF-1228" by General Electric.

As alkyldimethicone-copolyol which can be used in the emulsion according to the invention, lauryldimethicone-copolyol can be used, for example such as the product sold under the name "Q2-5200" by Dow Corning, and cetyldimethicone-copolyol, for example such as the product sold under the name "Abil EM 90" by Goldschmidt.

Other dimethicone-copolyols and alkyldimethicone-copolyols which may be used in the present invention are listed in *International Cosmetic Ingredient Dictionary and Handbook*, Volume 2, pages 1593–1595 (Seventh Edition, published by The Cosmetic, Toiletry, and Fragrance Association, 1997), incorporated herein by reference.

The emulsifiers are, for example, present in the emulsion according to the invention in a concentration ranging from 0.5 to 25%, and preferably from 5 to 20%, when they are used alone. These ranges include all specific values and subranges therebetween, including 1, 2, 3, 8,10,12,15, 18 and 22% by weight.

The emulsifiers used in the emulsion of the invention can also be combined with at least one coemulsifier such as, in particular, polyglyceryl tetraisostearate or polyglyceryl trioleate. Other suitable co-emulsifiers which may be used in the present invention are listed in *International Cosmetic Ingredient Dictionary and Handbook*, Volume 2, pages 1679–1686 (Seventh Edition, published by The Cosmetic, Toiletry, and Fragrance Association, 1997), incorporated herein by reference.

When the content of emulsifier is less than 2.5% of the total weight of the emulsion, it is preferable to add a co-emulsifier. When it is present, the co-emulsifier is used in a proportion of from 1 to 10 times the weight amount of the emulsifier. These ranges include all specific values and subranges therebetween, including 2,3, 5, 7 and 8 times the weight of the emulsifier.

Advantageously, the respective concentrations of emulsifiers and co-emulsifiers range from 0.5 to 10% and from 3 to 7% of the total weight of the emulsion. These ranges include all specific values and subranges therebetween, including 1, 1.5, 2, 2.5, 3.5, 4, 5, and 6% by weight.

For temperatures above 20° C. and/or for storage periods of several months, it is preferred to use a fully oxyethylenated alkyldimethicone-copolyol, and more especially cetyldimethicone-copolyol, as emulsifier.

Any suitable basic agent can be used to adjust the pH of the emulsion, and in particular inorganic bases such as alkali metal hydroxides (sodium hydroxide and potassium hydroxide) or ammonium hydroxides, and organic bases, in particular amphoteric bases, i.e. bases having both anionic and cationic functional groups.

The amphoteric bases can be primary, secondary, tertiary or cyclic organic amines and more preferably amino acids. Examples of amphoteric bases include, for example, glycine, lysine, arginine, taurine, histidine, alanine, valine, cysteine, trihydroxymethylaminomethane (TRISTA) and triethanolamine.

One or more basic agents can be used. The amount of basic agent(s) must be sufficient to bring the pH of the emulsion to between 5.5 and 7.5 and preferably to pH 6. The pH of the aqueous phase of the emulsion may be 5.6, 5.7, 5.8, 5.9, 6.1, 6.2, 6.3, 6.4, 6.5, 6.6, 6.7, 6.8, 6.9, 7.0, 7.1, 7.2, 7.3 or 7.4. The amount of the basic agent may range from, for example, from 0.1 to 10% and preferably from 0.5 to 3% of the total weight of the emulsion. These ranges include all specific values and subranges therebetween, including 0.2, 1, 2, 5 and 8% by weight.

Instead of adding a basic agent, ascorbic acid can be incorporated into the emulsion directly in salt form, and for example in the form of an alkali- metal, ammonium or organic-based salt. As salt, mention may be made, for example, of sodium ascorbate or calcium ascorbate.

Moreover, a small amount of an acid which allows a buffer effect to be obtained, such as citric acid, can be added to the basic agent. This acid can be used, for example, in an amount ranging from 0.1 to 5% of the total weight of the emulsion. This ranges include all specific values and subranges therebetween, including 0.2, 0.5, 1, 2, 3 or 4% by weight.

According to the invention, the aqueous phase of the emulsion can represent from 25 to 90%, and preferably from 45 to 80%, of the total weight of the emulsion. These ranges include all specific values and subranges therebetween, including 30, 35, 40, 50, 55, 65, 70, 75 and 85% by weight.

The aqueous phase of the emulsion can also contain an electrolyte such as, for example, an inorganic salt, e.g., sodium chloride or potassium chloride, so as to further improve the stability of the emulsion. The electrolyte content in the emulsion can range from 0 to 3% and preferably from 0.5 to 2% of the total weight of the emulsion. These ranges include all specific values and subranges therebetween, including 0.1, 0.2, 0.8, 1, 1.5 or 2.5% by weight.

Advantageously, and in order especially to avoid the presence in the aqueous phase of heavy metals which can catalyze the degradation of ascorbic acid, the aqueous phase is formed of exchanged or deionized water.

In order to further improve the stability of ascorbic acid over time, the emulsion of the invention can comprise a metal-sequestering agent such as a phosphoric acid derivative. The phosphoric acid derivatives which can be used in the invention are chosen in particular from ethylenediaminetetra(methylenephosphonic acid), hexamethylene-diaminetetra-(methylenephosphonic acid) and diethylenetriaminepenta(methylenephosphonic acid) and their salts, and in particular their sodium salts, such as the pentasodium salt of ethylenediaminetetra-(methylenephosphonic acid). Other suitable metal-sequestering agents which may be used in the present invention are listed in International Cosmetic Ingredient Dictionary and Handbook, Volume 2, page 1626 (Seventh Edition, published by The Cosmetic, Toiletry, and Fragrance Association, 1997), incorporated herein by reference.

Advantageously, ethylenediaminetetra (methylenephosphonic acid) is used, in particular the product sold by Monsanto under the name Dequest 2041. The pentasodium salt of this acid, which is sold under the name Dequest 2046 by Monsanto, can also be used advantageously. As another sequestering agent which can be used in the emulsion of the invention, mention may be made of diethylenetriaminepentaacetic acid, sold for example by Sigma.

When it is present, the sequestering agent is in a concentration generally ranging from 0.005 to 0.2% of the total weight of the emulsion. These ranges include all specific values and subranges therebetween, including 0.008, 0.01, 0.02, 0.05, 0.1 and 0.15% by weight.

According to the invention, the oily phase of the emulsion can represent from 3 to 75% and preferably from 5 to 30% of the total weight of the emulsion. These ranges include all specific values and subranges therebetween, including 4, 10, 15, 20, 25, 35, 40, 50 and 60% by weight.

The oily phase of the emulsion of the invention can contain oils and fatty substances of any kind that are known to those skilled in the art, such as mineral oils (paraffin, petroleum jelly), oils of plant origin (almond oil, apricot oil, jojoba oil), synthetic oils (perhydrosqualene, hydrogenated polyisobutene) and volatile or non-volatile silicone oils. Other suitable materials which may be used to form the oily phase are listed in *International Cosmetic Ingredient Dictionary and Handbook*, Volume 2, pages 1565–1570 and 1593–1595 (Seventh Edition, published by The Cosmetic, Toiletry, and Fragrance Association, 1997), incorporated herein by reference.

Preferably, the oily phase of the emulsion of the invention comprises at least one volatile silicone oil generally in a proportion of from 3 to 15% of the total weight of the emulsion, such as, for example, a cyclic silicone oil such as cyclopentadimethylsiloxane or cyclohexadimethylsiloxane. This range includes all specific values and subranges therebetween, including 4, 5, 8, 10 and 12% by weight. The oily phase may also comprise a non-volatile silicone oil such as, for example, phenyltrimethicone such as "Dow Corning 556 Fluid" sold by Dow Corning. According to a particular embodiment of the invention, the oily phase of the emulsion consists entirely of silicone oil.

The oily phase can also comprise fatty substances other than oils, chosen from fatty alcohols, fatty acids, waxes and resins (for example silicone resin).

The oily phase can also comprise a gelling agent. As the gelling agent, mention may be made of modified clays such as bentones, metal salts of fatty acids such as aluminum stearates, and hydrophobic silica. The gelling agent for the oily phase can be present in a concentration ranging, for example, from 1 to 15%, preferably 3 to 7%, of the total weight of the emulsion. These ranges include all specific values and subranges therebetween, including 2, 4, 5, 10 and 12% by weight.

According to a particular embodiment of the invention, the emulsion contains polyols in a sufficient amount to further improve the stability of the ascorbic acid. The polyols can be chosen, for example, from glycerol, glycols such as propylene glycol and PEG 8, and silicones containing hydroxyl groups. The polyols are present in an amount preferably ranging from 0.5 to 30%, and more preferably from 10 to 25%, of the total weight of the emulsion. These ranges include all specific values and subranges therebetween, including 1, 2, 5, 15 and 20% by weight.

In a known manner, the emulsion of invention can also contain additives that are common in the cosmetics and dermatological fields, such as hydrophilic or lipophilic active agents other than ascorbic acid, preserving agents, antioxidants, solvents, fragrances, fillers, screening agents, odor absorbers and dyestuffs, provided that the additive does not destabilize the ascorbic acid in the emulsion. The amounts of these various additives are those used conventionally in the fields considered, and, for example, from 0.01 to 15% of the total weight of the composition. This range includes all specific values and subranges therebetween, including 0.02, 0.05, 1, 2, 3, 5, 8, 10 and 12% by weight.

Depending on their nature, these additives can be introduced into the fatty phase or into the aqueous phase.

As filler, mention may be made, for example, of nylon and starch and its derivatives.

As hydrophilic active agents, it is possible to use, for example, besides the polyols indicated above, proteins or protein hydrolyzates, sodium pyrrolidonecarboxylate, NMFs (normal moisturization factors), hyaluronic acid, amino acids, allantoin, sugars and sugar derivatives, and starch.

As lipophilic active agents, it is possible to use, for example, tocopherol (vitamin E) and its derivatives, essential fatty acids, ceramides and essential oils.

Advantageously, the composition of the invention comprises, on a weight basis:
from 0.01 to 20% of ascorbic acid,
from 0.5 to 25% of dimethiconecopolyol,
from 0.1 to 10% of silicone oil,
from 0.005 to 0.2% of pentasodium salt of ethylenediaminetetra(methylene-phosphonic acid), and
from 0.1 to 10% of sodium hydroxide.

As already mentioned above, however minimal the degradation of the ascorbic acid, this results in yellowing of the composition containing it. Accordingly, it is preferable, in order to avoid this yellowing, for the emulsion according to the invention to be packaged so as not to be in contact with oxygen and to be sheltered from light.

Thus, the emulsion of the invention is preferably prepared under inert atmosphere (nitrogen or a rare gas such as argon), free of any oxygen or containing less than 3% v/v of oxygen, and under inactinic light, such as that of a sodium vapor lamp.

Advantageously, the emulsion of the invention is packaged in the presence of an oxygen absorber such as, for example, the oxygen absorber "Atco" sold by Standa Industries. The oxygen absorber is preferably separated from the emulsion by a gas-porous, liquid-impermeable membrane, such as the one described in document FR-A-2,671,055, incorporated herein by reference.

Even more preferably, the emulsion of the invention is packaged in a container on which is mounted a device for distribution without uptake of air, for example such as the one described in document FR-A-2,666,308, incorporated herein by reference.

The present invention also provides a cosmetic and/or dermatological composition comprising an emulsion as defined above.

For a cosmetic and/or dermatological application, the emulsion according to the invention must contain a topically acceptable medium, i.e. one which is compatible with the skin, mucous membranes and/or the hair. The composition based on this emulsion can in particular constitute cleansing, protective, treatment or care compositions for the skin and/or the hair, in particular for the face, for the neck for the hands, for the hair, for the scalp or for the body, as well as for the eyelashes.

Another subject of the invention is the use of the cosmetic composition according to the above invention for the cosmetic treatment of the skin, and in particular for smoothing out fine lines on the skin, for tonifying and regenerating the skin, for improving the complexion, removing skin pigmentation marks, for combating the harmful effects of UV radiation, and/or for generally strengthening skin tissues against environmental attack (pollution).

The subject of the invention is also the use of the above emulsion for the manufacture of a cream intended for a dermatological treatment of the skin.

Lastly, the subject of the invention is a cosmetic process for treating the skin, this process consisting in applying a cosmetic composition in accordance with the invention to the skin, including the area around the eyes.

Having generally described this invention, a further understanding can be obtained by reference to certain specific examples which are provided herein for purposes of illustration only and are not intended to be limiting unless otherwise specified. The amounts therein are given as a % by weight, except where otherwise mentioned.

EXAMPLES

Example 1

Face Cream

| | |
|---|---|
| Mixture of dimethiconecopolyol and cylcomethicone Q2-3225C from Dow Corning) | 20% |
| Phenyltrimethicone (Dow Corning 556 Fluid) | 4% |
| Plant oil | 3% |
| Glycerol | 23% |
| Propylene glycol | 6% |
| Sodium hydroxide acid | 1.83% |
| Citric acid | 1.24% |
| Ascorbic acid | 5% |
| Deionized water | qs 100% |

The emulsion obtained has a pH of 6. It is in the form of a cream which is suitable for facial care and is gentle to apply. This cream gives an immediately radiant complexion and smooths out imperfections.

Moreover, the ascorbic acid in this emulsion shows a degradation of 8% after two months at 45° C.

Comparative Example 1

A comparative example was carried out by replacing, in Example 1, the citric acid and hydroxide with water. In this case, the pH of emulsion obtained is 2.8. This emulsion shows a degradation of 17% after two months at 45° C.; this degradation is thus considerably larger than that of the emulsion at pH 6.

Example 2

Face Cream

| | |
|---|---|
| Mixture of dimethiconecopolyol and cyclomethicone (Q2-3225C from Dow Corning) | 8% |
| Phenyltrimethicone (Dow Corning 556 Fluid) | 15% |
| Tocopherol | 0.5% |
| Propylene glycol | 10% |
| PEG-8 | 8% |
| Glycerol | 2.4% |
| Pentasodium salt of ethylenediamine-tetra(methylenephosphonic acid) at 33% in water | 0.1% |
| Sodium hydroxide | 1.24% |
| Citric acid | 1.24% |
| Ascorbic acid | 5% |
| Deionized water | qs 100% |

This facial care cream is light and soft. It gives an immediately radiant complexion and allows imperfections to be smoothed out.

Moreover, the ascorbic acid it contains suffered a degradation of 8% after two months at 45° C.

Obviously, numerous modifications and variations of the present invention are possible in light of the above teachings. It is therefore to be understood that within the scope of the appended claims, the invention may be practiced otherwise than as specifically described herein.

The French Priority Application, French Application Serial No. 97-10902, filed Sep. 2, 1997, is incorporated herein by reference in its entirety.

What is claimed is:

1. A water-in-oil emulsion, comprising:
   a) an aqueous phase dispersed in an oily phase, wherein the aqueous phase has a pH of from 6.1 to 7.5;
   b) at least one silicone-based emulsifier which consists essentially of partially or fully oxyethylenated polyether groups;
   c) ascorbic acid or a salt thereof;
   d) at least one volatile silicone oil in an amount of 3 to 15% of the total weight of the emulsion, wherein said volatile silicone oil is selected from the group consisting of cyclopentadimethylsiloxane and cyclohexadinietbylsiloxane; and
   e) a non-volatile silicone oil, which is phenyltrimethicone.

2. The water-in-oil emulsion of claim 1, wherein the aqueous phase has a pH of from 6.2 to 7.4.

3. The water-in-oil emulsion of claim 1, which comprises 0.1 to 10% by weight of the ascorbic acid or a salt thereof.

4. The water-in-oil emulsion of claim 1, wherein the pH of the aqueous phase is adjusted using at least one basic agent selected from the group consisting of inorganic bases and organic bases.

5. The water-in-oil emulsion of claim 4, which comprises from 0.1 to 10% by weight of the basic agent.

6. The water-in-oil emulsion of claim 1, which comprises a salt of ascorbic acid.

7. The water-in-oil emulsion of claim 1, which further comprises citric acid.

8. The water-in-oil emulsion of claim 1, which comprises 25 to 90% by weight of the aqueous phase.

9. The water-in-oil emulsion of claim 1, wherein the silicone-based emulsifier is selected from the group consisting of dimethiconecopolyols and alkyldimethiconecopolyols.

10. The water-in-oil emulsion of claim 1, further comprising a co-emulsifier, wherein the amount of the co-emulsifier is from 1 to 10 times the amount of weight of the silicone-based emulsifier.

11. The water-in-oil emulsion of claim 1, which comprises 0.5 to 25% by weight of the silicone-based emulsifier.

12. The water-in-oil emulsion of claim 1, further comprising a metal-sequestering agent.

13. The water-in-oil emulsion of claim 1, wherein the sequestering agent is the pentasodium salt of ethylenediaminetetra(methylenephosphonic acid).

14. The water-in-oil emulsion of claim 1, wherein the silicone-based emulsifier is a compound containing at least one silicone moiety therein.

15. The water-in-oil emulsion of claim 1, wherein the silicone-based emulsifier comprises a fully oxyethylenated alkyldimethicone-copolyol.

16. The water-in-oil emulsion of claim 15, wherein the silicone-based emulsifier comprises a fully oxyethylenated cetyldimethicone-copolyol.

17. The water-in-oil emulsion of claim 1, wherein the oil phase of the emulsion comprises from 3 to 75% of the total weight of the emulsion.

18. The water-in-oil emulsion of claim 1, wherein said oily phase consists entirely of silicone oil.

19. A cosmetic or dermatological composition, comprising the water-in-oil emulsion of claim 1.

20. A method of tonifying and regenerating skin, smoothing out lines on the skin, improving skin complexion, removing skin pigmentation marks, combating harmful effects of UV radiation, or strengthening skin tissues against environmental attack, or a combination of the above, which comprises applying an effective amount of the water-in-oil emulsion of claim 1 to the skin.

21. The method of claim 20, wherein the water-in-oil emulsion in applied to the skin around the eyes.

22. A method of stabilizing ascorbic acid or salts thereof, which comprises:
   incoiporating ascorbic acid or a salt thereof into the water-in-oil emulsion of claim 1.

23. The method of claim 22, wherein the emulsion comprises 0.1 to 10% by weight of the ascorbic acid or a salt thereof.

24. The method of claim 22, wherein the silicone-based emulsifier is selected from the group consisting of dimethiconecopolyols and alkyldimethiconecopolyols.

25. The method of claim 24, wherein the silicone-based emulsifier comprises a fully oxyethylenated alkyldimethicone-copolyol.

26. The method of claim 25, wherein the silicone-based emulsifier comprises of fully oxyethylenated alkyldimethicone-copolyol.

* * * * *

UNITED STATES PATENT AND TRADEMARK OFFICE
CERTIFICATE OF CORRECTION

PATENT NO.   : 6,239,174 B1
DATED        : May 29, 2001
INVENTOR(S)  : Isabelle Afriat et al.

It is certified that error appears in the above-identified patent and that said Letters Patent is hereby corrected as shown below:

Column 8,
Lines 18-19, "cyclobexadini-etbylsiloxane" should read -- cyclohexadimethylsiloxane --;
Line 49, "claim 1" should read -- claim 12 --.

Column 9,
Line 9, "emulsion in applied" should read -- emulsion is applied --;
Line 12, "incoiporating" should read -- incorporating --.

Signed and Sealed this

Fifteenth Day of January, 2002

JAMES E. ROGAN
*Director of the United States Patent and Trademark Office*

*Attest:*

*Attesting Officer*